(12) United States Patent
Wemken et al.

(10) Patent No.: US 7,323,686 B2
(45) Date of Patent: Jan. 29, 2008

(54) SENSOR FOR MONITORING THE IMMEDIATE VICINITY OF A MOTOR VEHICLE

(75) Inventors: Frank Wemken, Weinsheim (DE); Edmund Leis, Mainz (DE)

(73) Assignee: Delphi Technologies, Inc., Troy, MI (US)

( * ) Notice: Subject to any disclaimer, the term of this patent is extended or adjusted under 35 U.S.C. 154(b) by 118 days.

(21) Appl. No.: 11/282,135

(22) Filed: Nov. 18, 2005

(65) Prior Publication Data

US 2007/0138393 A1 Jun. 21, 2007

(30) Foreign Application Priority Data

Nov. 18, 2004 (DE) ............... 10 2004 055 680

(51) Int. Cl.
*G01J 5/00* (2006.01)
(52) U.S. Cl. ............... 250/338.1; 250/252.1; 250/336.1
(58) Field of Classification Search ............ 250/336.1, 250/338.1, 252.1
See application file for complete search history.

(56) References Cited

U.S. PATENT DOCUMENTS 6,189,808 B1 * 2/2001 Daniels et al. ........... 239/284.2
6,768,103 B2 * 7/2004 Watson .................... 250/252.1

* cited by examiner

*Primary Examiner*—David Porta
*Assistant Examiner*—Mark R Gaworecki
(74) *Attorney, Agent, or Firm*—David P. Wood

(57) ABSTRACT

A sensor for monitoring the immediate vicinity of a motor vehicle comprises an infrared emitter that is arranged behind a lens and a receiver for reflected infrared radiation, as well as an evaluation unit for detecting the presence of an object in the immediate vicinity of the motor vehicle, wherein a signal can be forwarded from the evaluation unit to a control device in the motor vehicle. In order to also ensure the proper function of the sensor when the lens is soiled, an infrared emitter and a receiver are provided for measuring the transparency of the lens, wherein the evaluation unit is able to increase the power of the infrared emitter for monitoring the immediate vicinity of the motor vehicle if it determines that the lens transparency is reduced.

12 Claims, 3 Drawing Sheets

SENSOR FOR MONITORING THE IMMEDIATE VICINITY OF A MOTOR VEHICLE

Figure 1:
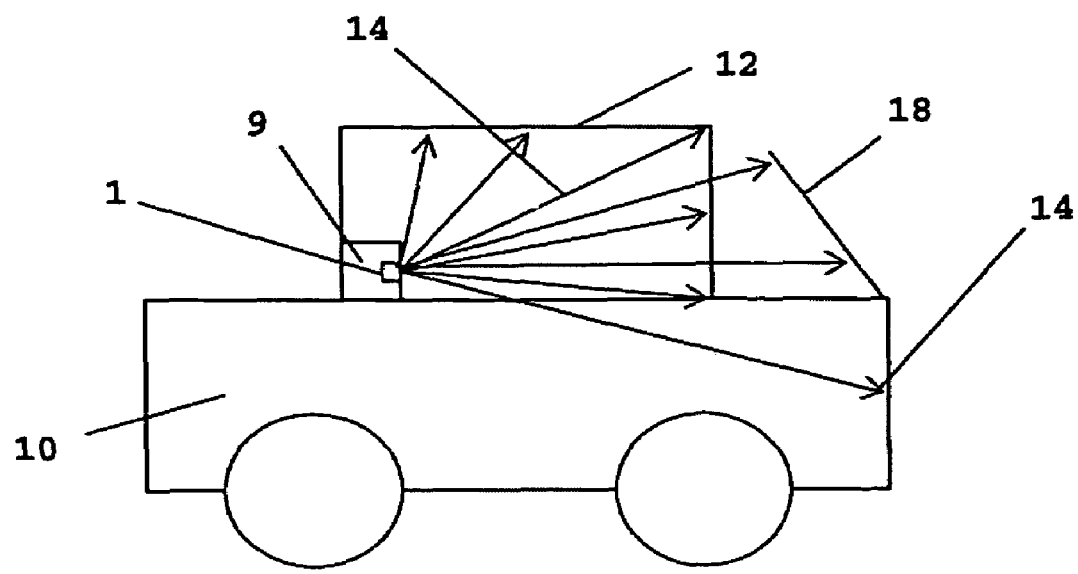

The invention pertains to a sensor for monitoring the immediate vicinity of a motor vehicle, wherein said sensor comprises an infrared emitter that is arranged behind a lens and a receiver for reflected infrared radiation, as well as an evaluation unit for detecting the presence of an object in the immediate vicinity of the motor vehicle, wherein a signal can be forwarded from the evaluation unit to a control device in the motor vehicle.

Modern convertibles or roadsters are, equipped with electrically actuated convertible tops. Convertible tops of fabric or folding tops of metal and/or plastic are closed by the user, e.g., when parking and exiting the motor vehicle. This can be achieved by actuating an operating element on the dashboard of the motor vehicle. Alternatively, the user can control the corresponding electric motors for actuating the convertible top by means of a remote control integrated into the motor vehicle key after exiting the motor vehicle. This remote control transmits signals to a receiver in the motor vehicle by means of infrared radiation, electromagnetic waves or ultrasonic pulses, said signals then being forwarded to a central control device in the motor vehicle that controls all functions. The control device subsequently actuates the electric motors for closing the convertible top. The convertible top can be opened in the reverse sequence when the user returns to and intends to reenter the motor vehicle.

When the convertible top is closed after exiting the motor vehicle, the user frequently departs the immediate vicinity of the motor vehicle while the convertible top closes because no additional manipulations by the user are required for closing the convertible tops of modern motor vehicles. This means that the user no longer monitors the proper closing of the convertible top. In instances in which the user has already departed the immediate vicinity of the motor vehicle while the convertible top closes, it is possible for a person or, if the motor vehicle is parked in a forested area, an animal to approach the motor vehicle and, for example, for a person's hand to become trapped between the closing convertible top and the upper edge of the front windshield. This can occur, in particular, if a child coincidentally passes the motor vehicle. Although most electric motors for actuating convertible tops are equipped with an automatic shut-off that is activated when a certain load is exceeded, a person may still be injured by the closing or opening convertible top.

This problem is prevented with the aid of sensors for monitoring the immediate vicinity of a motor vehicle. These sensors essentially consist of an infrared emitter that emits infrared radiation into the immediate vicinity around the motor vehicle, for example, over a lateral range of one to two meters along one side of the motor vehicle. A so-called infrared curtain can be produced, e.g., along one longitudinal side of the motor vehicle, with infrared emitters such as are usually arranged behind a protective lens of glass or a suitable plastic material. As soon as a person, an animal or another moving object penetrates this infrared curtain while the convertible top is opened or closed, said object reflects the infrared radiation so that it can be detected by a receiver for reflected infrared radiation associated with the sensor. This receiver is also arranged behind the lens. The sensor is also provided with an evaluation unit that determines whether a moving object has entered the immediate vicinity of the motor vehicle to be monitored, in particular, based on the intensity of the signal received by the receiver. If an approaching object is detected by the evaluation unit, a corresponding signal is forwarded, for example, to the central control device in order to subsequently interrupt the opening or closing of the convertible top and to prevent a person having entered the immediate vicinity of the motor vehicle from being injured. In this case, an optical and/or acoustical warning signal may be simultaneously generated to urge the person to step away from the motor vehicle. It would also be conceivable, for example, to inform the user of the interruption in the opening or closing of the convertible top by transmitting a radio signal to the remote control.

When a motor vehicle is used outside the conventional road network, the body of the motor vehicle may be subjected to significant soiling, for example, when driving through mud puddles or the like. This can also lead to dirt deposits on the lens of the sensor for monitoring the immediate vicinity of the motor vehicle. In such instances, the infrared radiation can penetrate this dirt layer only partially, if it all, and reflected infrared radiation can no longer be reliably detected by the receiver. This impairs the proper function of the sensor such that persons can be injured when the convertible top is opened or closed, despite the sensor.

The invention is based on the objective of developing a sensor of the initially described type for monitoring the immediate vicinity around a motor vehicle, wherein said sensor also makes it possible to reliably monitor the immediate vicinity around the motor vehicle when the body of the motor vehicle is soiled.

According to the invention, this objective is attained by providing an infrared emitter and a receiver for measuring the transparency of the lens, wherein the power of the infrared emitter for monitoring the immediate vicinity of the motor vehicle can be increased by the evaluation unit if it is determined that the lens transparency is reduced.

The invention essentially proposes to transmit infrared radiation emitted by an infrared emitter through the lens. The refraction of the electromagnetic infrared waves at the transition from the lens to the surrounding atmosphere causes a small portion of the electromagnetic infrared waves to be reflected at this boundary surface back into the sensor. A receiver for the infrared radiation reflected at the boundary surface is provided in the sensor and can measure the intensity of this reflected radiation. A nominal value for the proportion of infrared radiation reflected when the lens is clean can be stored in the associated evaluation unit, if so required, with corresponding tolerance values. The measurement signal of the receiver is compared with this stored value in the evaluation unit. If the signal of the receiver lies below the tolerance limits, the lens is categorized as non-soiled, and the sensor for monitoring the immediate vicinity of the motor vehicle operates in the normal mode. The proportion of infrared waves reflected is increased if the lens is soiled because the deposited dirt usually reflects the infrared radiation rather than transmitting it outward. A soiled lens results in an increase in the proportion of reflected infrared waves that can be detected by the receiver, with the lens being categorized as soiled by the evaluation unit in this case.

In such instances, the evaluation unit increases the infrared radiation emitting power of the infrared emitter used for monitoring the immediate vicinity around a motor vehicle, namely until the normal sensor capacity is restored. In this case, the evaluation unit can determine by how much the power of the infrared emitter needs to be increased in order to compensate for the soiled lens based on the degree of soiling, i.e., the increase in the proportion of the infrared radiation that is reflected.

The scope of the invention also includes embodiments in which the infrared radiation for determining the degree of lens soiling as well as the infrared radiation for monitoring the immediate vicinity around the motor vehicle are emitted by the same infrared emitter. For example, the infrared emitter can successively operate in two different operating modes. Radiation of reduced intensity for determining the degree of lens soiling is initially emitted in this case, and the actual infrared radiation for monitoring the immediate vicinity around the motor vehicle is emitted subsequently. Analogously, the receiver can initially receive the infrared radiation reflected at the transition from the lens to the surrounding atmosphere and then the infrared radiation reflected by objects that may be situated within the immediate vicinity of the motor vehicle. However, these functions are preferably fulfilled by different infrared emitters and receivers, as described below.

The advantage of the invention can be seen in that soiling of the sensor or its lens can be reliably detected such that an increase in the power of the infrared emitter makes it possible to emit and receive infrared radiation of sufficient intensity in the subsequent monitoring mode. Consequently, the utilization of such a sensor also makes it possible to ensure the safe opening and closing of a convertible top if the body of the respective vehicle is significantly soiled.

According to one advantageous embodiment, the power of the infrared emitter can be increased by up to 40% relative to a normal operating mode with a clean lens. The infrared emitter naturally has a capacity sufficient to allow adjustment to achieve emission of higher-entensity infrared radiation by the evaluation unit. If the lens is soiled to such a degree that this increase in power is insufficient to produce an infrared curtain of the required intensity, the evaluation unit can transmit a signal to the central control device for interrupting the opening or closing of the convertible top, e.g., by means of conventional data bus architectures known from automotive engineering.

A separate infrared emitter for measuring the transparency of the lens is preferably provided in the sensor. For example, an infrared emitter of low capacity may be used for this purpose because it is required merely to measure the reflectivity at the transition from the lens to the surrounding atmosphere. This also allows a quasi-parallel operation; i.e., a separate infrared emitter initially measures the degree of lens soiling either when the sensor is switched on or at predetermined intervals in order to increase, if so required, the power of the infrared emitter used to monitor the immediate vicinity of the motor vehicle. After this measurement, the immediate vicinity of the motor vehicle is monitored, if applicable, with a correspondingly adjusted power of the infrared emitter. The invention in particular proposes to provide several infrared emitters for measuring the transparency of the lens such that the cleanliness of the lens can be monitored at different locations.

Analogously, a separate receiver for measuring the transparency of the lens is provided in the sensor in order also to realize a quasi-parallel operation in this respect. It would also be conceivable to provide several receivers of this type for monitoring the cleanliness of the lens at different locations.

In one configuration of the sensor, a receiving section and a transmitting section of the sensor are respectively provided with an infrared emitter and a corresponding receiver. This makes it possible to separately detect soiling of the lens in the respective sections of the sensor.

When the transparency of the lens is measured, the evaluation unit preferably adjusts the power of the infrared emitter of the transmitting section and the infrared emitter of the receiving section to a lower value than in the normal operating mode. This means that soiling of the lens in the transmitting section and/or receiving section of the sensor leads to a reflection of the respectively emitted infrared waves to the corresponding receiver. According to one additional refinement of the invention, the evaluation unit, based on the measurement of the lens transparency, adjusts the power of the infrared emitter of the transmitting section to a corresponding or higher value than that in the normal operating mode. This ensures that an object situated in the immediate vicinity of the motor vehicle can also be detected if the lens is slightly soiled.

Advantageously, the receiver for the infrared radiation reflected at the lens and/or reflected outside the sensor by an object in each case consists of a photodiode. A person skilled in the art is familiar with photodiodes of this type as well as the design options for realizing the respectively desired sensitivities for monitoring the different types of reflected infrared radiation.

The reliability of the sensor can be increased, for example, by providing the respective individual components, i.e., the infrared emitters, the receivers and the evaluation unit, with a temperature stabilization circuit. This means that the measurement results cannot be falsified by temperature fluctuations or the heating of individual components in the continuous operating mode.

In order to optimally monitor the immediate vicinity around a motor vehicle, particularly along a longitudinal side thereof, the sensor is preferably integrated into the exterior rearview mirror of the motor vehicle and produces, for example, an infrared curtain along the corresponding side of the motor vehicle, rearward from the exterior rearview mirror relative to the driving direction. In this case, the sensor is arranged, in particular, underneath the reflective surface of the exterior rearview mirror, and is installed into mirror's housing.

If the evaluation unit determines that the lens is soiled and increases the power of the infrared emitter accordingly, the control device in the motor vehicle may simultaneously generate a warning signal in order to inform the user of the soiled lens. This may be realized optically or acoustically, for example, by flashing the blinkers or by generating a voice message. It would also be conceivable to generate a corresponding warning signal in the remote control carried by the user.

Upon determining that the lens is soiled, the evaluation unit could also activate a cleaning device associated with the sensor, e.g., a spray nozzle for water and/or a lens wiper system, in order to clean the lens.

It goes without saying that the above-disclosed characteristics as well as the characteristics disclosed below are suitable for use not only in the respectively described combination, but also in other combinations. The scope of the invention is defined by the claims only.

Figure 2:
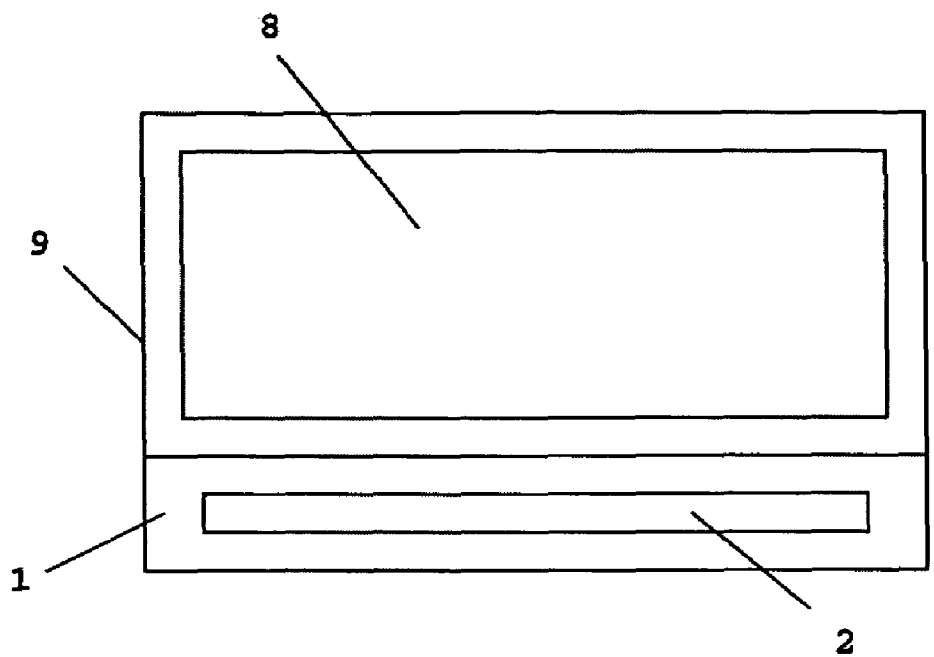
Figure 3:
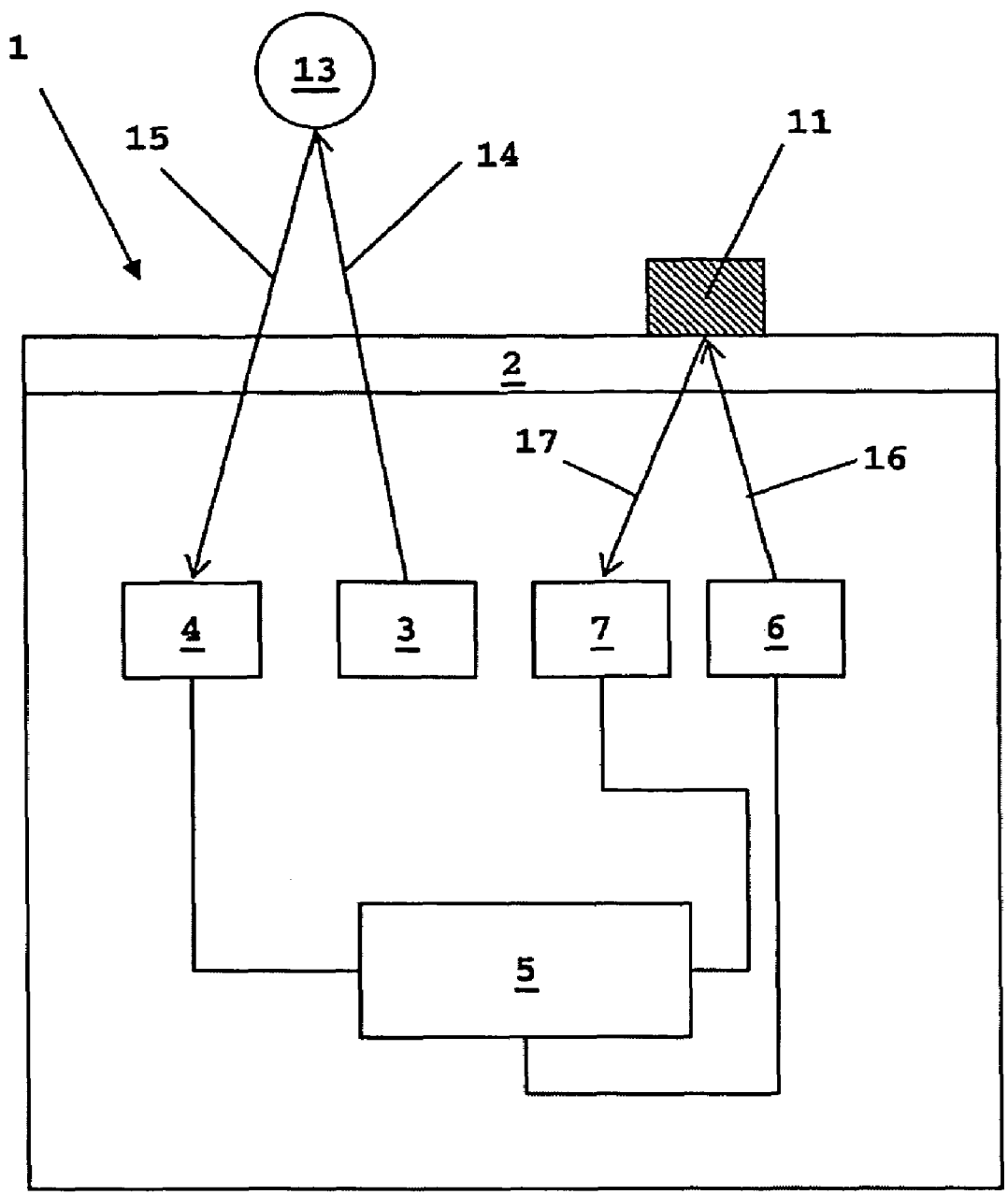

The invention is described in greater detail below with reference to two embodiments that are illustrated in the figures. The figures show:

FIG. 1, a schematic side view of a motor vehicle with an exterior rearview mirror, and with a sensor according to the invention integrated therein;

FIG. 2, an enlarged front view of the exterior rearview mirror according to FIG. 1;

FIG. 3, an enlarged detail of the sensor according to FIG. 1, and

Figure 4:
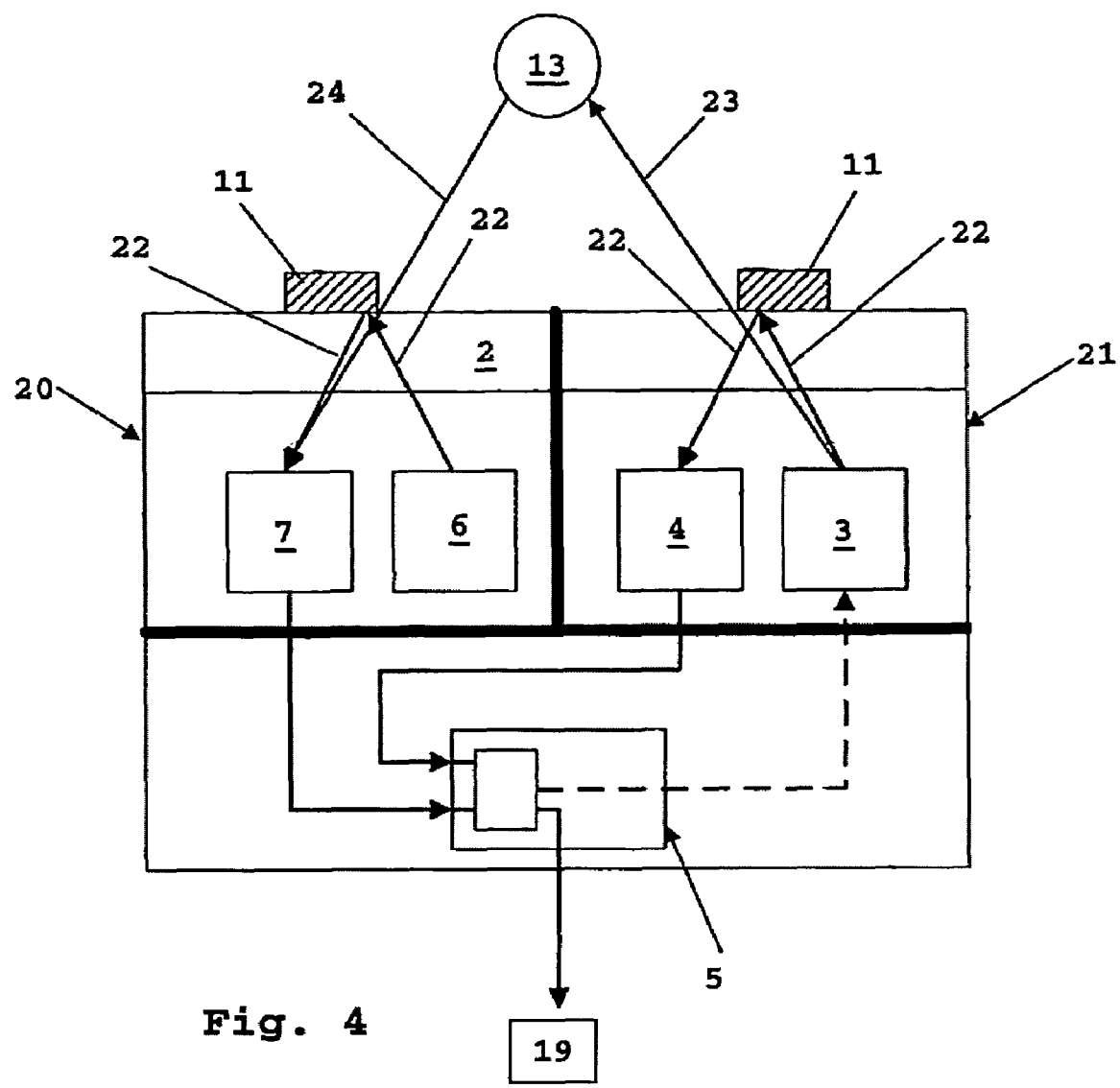

FIG. 4, an enlarged detail of an alternative variation of the sensor according to FIG. 1.

The motor vehicle 10 is equipped with an exterior rearview mirror 8 that is arranged in a housing 9. A sensor 1 for monitoring the immediate vicinity of the motor vehicle 10 is also integrated into the housing 9. As indicated with arrows 14, this sensor 1 emits infrared radiation in order to detect the presence of an object 13 in the immediate vicinity of the motor vehicle to be monitored by the sensor 1. For this purpose, the sensor 1 is equipped with a receiver 4 for measuring the infrared radiation that is emitted by the infrared emitter 3 contained in the sensor 1, and that is reflected by the object 13. If the evaluation unit 5 in the sensor 1 determines the presence of an object 13 in the immediate vicinity of the motor vehicle, the opening or closing of a convertible top 12 or of a convertible top cover lid 18 on the rear side of the motor vehicle 10 is interrupted, in particular to prevent persons from being injured by the opening or closing convertible top 12 or the convertible top cover lid 18. The sensor 1 is arranged in the housing 9 underneath the exterior rearview mirror 8 and is equipped with a lens 2 that is transparent to infrared radiation. This arrangement of the sensor 1 makes it possible to monitor the lateral region of the motor vehicle 10.

FIG. 3 shows the basic design of the sensor 1 for monitoring the immediate vicinity of a motor vehicle 10. The sensor 1 comprises the infrared emitter 3 for emitting infrared radiation of sufficient intensity for monitoring the immediate vicinity of the motor vehicle. The infrared emitter 3 is provided with a receiver 4 for measurement the infrared radiation reflected by the object 13, as indicated with arrows 14, 15. The measurement signal of the receiver 4 is fed to an evaluation unit 5 that subsequently determines the presence of an object 13 in the immediate vicinity of the motor vehicle, for example, based on an increase in the proportion of the infrared radiation reflected. The evaluation unit then forwards a signal for interrupting the opening or closing of the convertible top 12 to a central control device 19 in the motor vehicle 10.

Another infrared emitter 6 for monitoring the soiling of the lens 2 is also provided in the sensor 1. A slight reflection of the infrared radiation takes place at the transition from the lens 2 to the surrounding atmosphere, as indicated with arrows 16, 17. This reflected infrared radiation is measured by another receiver 7. If dirt 11 is deposited on the lens 2, e.g., in the form of mud splashes, the reflectivity at the boundary between the lens 2 and the atmosphere changes such that the receiver 7 forwards a different measurement signal to the evaluation unit 5. The dirt deposits 11 also reduce the intensity of the infrared radiation emitted by the infrared emitter 3 for monitoring the immediate vicinity of the motor vehicle.

If the evaluation unit 5 determines the presence of dirt deposits 11, it increases the power of the infrared emitter 3 accordingly, by up to 40%. Consequently, the infrared radiation emitted by this emitter has sufficient intensity for monitoring the immediate vicinity of the motor vehicle 10 despite the presence of the dirt deposits 11. In other words, the reduction of the infrared radiation emitted by the infrared emitter 3 caused by the dirt deposits 11 on the lens 2 is compensated.

Sensor 1 shown in FIG. 4 has a receiving section 20 and a transmitting section 21, with each of which an infrared emitter 3, 6 and a receiver 4, 7 are respectively associated. The evaluation unit 5 adjusts each of the infrared emitters 3, 6 to a relatively low power in order to measure the dirt deposits 11 on the lens 2. As indicated with arrows 22, the infrared radiation emitted by the infrared emitters 3, 6 is reflected at the transition from the lens 2 to the surrounding atmosphere, and the reflected infrared radiation is measured by the corresponding receivers 4, 7 that subsequently transmit corresponding signals to the evaluation unit 5. If applicable, the evaluation unit 5 then determines that dirt deposits 11 are present on the lens 2 and increases the power of the infrared emitter 3 of the transmitting section 21 such that the infrared radiation (arrow 23) of this emitter has sufficient intensity for detecting the object 13. In this case, the infrared radiation reflected by the object 13 in accordance with the arrow 24 is measured by the receiver 7 in the receiving section 20.

It goes without saying that several infrared emitters 6 and/or receivers 7 may be provided the sensor 1 in order to monitor the cleanliness of the lens 2 at different locations.

LIST OF REFERENCE SYMBOLS

1 Sensor
2 Lens
3 Infrared emitter
4 Receiver
5 Evaluation unit
6 Infrared emitter
7 Receiver
8 Exterior rearview mirror
9 Housing
10 Motor vehicle
11 Dirt deposits
12 Convertible top
13 Object
14 Arrow
15 Arrow
16 Arrow
17 Arrow
18 Convertible top cover lid
19 Control device
20 Receiving section
21 Transmitting section
22 Arrow
23 Arrow
24 Arrow

The invention claimed is:

1. A sensor for monitoring the immediate vicinity of a motor vehicle, the sensor comprising:
   an infrared emitter that is arranged behind a lens;
   a receiver for reflected infrared radiation; and
   an evaluation unit for detecting the presence of an object in the immediate vicinity of the motor vehicle;
   wherein a signal can be forwarded from the evaluation unit to a control device in the motor vehicle;
   wherein an infrared emitter and a receiver are provided for measuring the transparency of the lens; and
   wherein the evaluation unit is configured to increase the power of the infrared emitter for monitoring the immediate vicinity of the motor vehicle if it is determined that the lens transparency is reduced.

2. The sensor according to claim 1, wherein the power of the infrared emitter can be increased by up to 40% relative to the normal operating mode.

3. The sensor according to claim 1 or 2, wherein the transparency of the lens is measured with one or more separate infrared emitters.

4. The sensor according to claim 1 or 2, wherein the transparency of the lens is measured with one or more separate receivers.

5. The sensor according to claim 1, wherein a receiving section and a transmitting section of the sensor each have an infrared emitter and a receiver.

6. The sensor according to claim 5, wherein the evaluation unit is configured to adjust, when the transparency of the lens is measured, a power of the infrared emitter of the transmitting section and of the infrared emitter of the receiving section to a lower power than that used in the normal operating mode.

7. The sensor according to claim 5 or 6, wherein, based on the result of the transparency measurement of the lens, the evaluation unit adjusts the power of the infrared emitter of the transmitting section to a value that corresponds to, or is higher than, that used in the normal operating mode.

8. The sensor according to claim 1 or 2, wherein the receiver comprises a photodiode.

9. The sensor according to claim 1 or 2, wherein the sensor is temperature-stabilized.

10. The sensor according to claim 1 or 2, wherein the sensor is integrated into a housing of an exterior rearview mirror of the motor vehicle.

11. The sensor according to claim 1 or 2, wherein the evaluation unit is configured to generate a warning signal.

12. The sensor according to claim 1 or 2, wherein the evaluation unit is configured to activate a cleaning device associated with the lens.

* * * * *